United States Patent
Hearn et al.

(10) Patent No.: US 7,302,567 B2
(45) Date of Patent: Nov. 27, 2007

(54) TECHNICAL FACILITY HAVING SOFTWARE STORED ON A COMPUTER OF THE TECHNICAL FACILITY

(75) Inventors: Andrea Hearn, Neunkirchen am Brand (DE); Wolfgang Herrmann, Herzogenaurach (DE); Detlef Hofmann, Erlangen (DE); Stephan Welsing, Hoechstadt (DE)

(73) Assignee: Siemens Aktiengesellschaft, Munich (DE)

( * ) Notice: Subject to any disclaimer, the term of this patent is extended or adjusted under 35 U.S.C. 154(b) by 709 days.

(21) Appl. No.: 10/324,342

(22) Filed: Dec. 19, 2002

(65) Prior Publication Data

US 2003/0135733 A1    Jul. 17, 2003

(30) Foreign Application Priority Data

Jan. 15, 2002   (DE) ................................ 102 01 326

(51) Int. Cl.
*H04L 12/22* (2006.01)
*H04L 9/32* (2006.01)
*H04L 12/26* (2006.01)

(52) U.S. Cl. ......................... 713/166; 713/167; 726/30

(58) Field of Classification Search ........ 713/166–167; 726/30
See application file for complete search history.

(56) References Cited

U.S. PATENT DOCUMENTS

| | | | |
|---|---|---|---|
| 5,363,446 A | | 11/1994 | Ruppertz et al. |
| 5,537,544 A | | 7/1996 | Morisawa et al. |
| 5,796,941 A | * | 8/1998 | Lita ............................. 726/29 |
| 2002/0152395 A1 | * | 10/2002 | Zhang et al. ................ 713/200 |
| 2002/0198748 A1 | * | 12/2002 | Eden et al. .................... 705/7 |

* cited by examiner

*Primary Examiner*—Gilberto Barron, Jr.
*Assistant Examiner*—Venkat Perungavoor
(74) *Attorney, Agent, or Firm*—Schiff Hardin LLP

(57) ABSTRACT

A technical facility has a computer with service software stored therein that has first, second and third service modules. The first service module has a first service routine or a first group of service routines that is available to an operator of the technical facility without a training for application of the first service routine or the first group of service routines. The second service module has a second service routine or a second group of service routines that is available to the operator only after a training. The third service module has a third service routine or a third group of service routines that is denied to the operator.

14 Claims, 2 Drawing Sheets

FIG. 2

| Service Module | License levels | Licensing fees |
|---|---|---|
| 21 | L1 | none |
| 22 | L2 | none |
|    | L3 | yes |
|    | L4 | yes |
|    | L5 | yes |
| 23 | L6 | Denied to the operator |

TECHNICAL FACILITY HAVING SOFTWARE STORED ON A COMPUTER OF THE TECHNICAL FACILITY

BACKGROUND OF THE INVENTION

1. Field of the Invention

The present invention is directed to a technical facility having service software stored on a computer of the technical facility 2. Description of the Prior Art As used herein, "technical facility" means a technical system such as, for example, a conveyor system or a technical apparatus such as, for example, a magnetic resonance apparatus. Service software is a computer program with which, in particular, maintenance or repair of the facility can be undertaken. In a computerized technical facility, the service software usually is stored on the computer that controls the technical facility. During repair or maintenance, i.e. during service performed at the technical facility, the service software supports the person implementing the service. If, for example, the technical facility is an X-ray apparatus or a computed tomography apparatus, a newly installed X-ray tube can be adjusted and tested with the assistance of the service software. The service software also can be specifically employed for detecting an error that may be presented in the technical facility.

For example, the service can be implemented for the operator of the technical facility by specifically trained personnel of the supplier or of the manufacturer of the technical facility. However, the service also can be implemented by a service technician of the operator of the technical facility. So that the operator's own service technician can efficiently operate the service software, this service technician may have to be suitably trained by the supplier or the manufacturer under certain circumstances. The supplier or the manufacturer also must make the service software accessible to the operator of the technical facility.

The service software also can be employed for routine activities such as, for example, regularly implemented quality measurements at a computed tomography apparatus. This type of service is normally not performed by a specifically trained service technician but by the person who normally operates the technical facility as intended. No special training is needed for this type of service; the service software, however, must likewise be accessible to the operator.

As a rule, an operator's own personnel as well as a manufacturer's personnel require access to the service software. Occasionally, well-trained personnel of the operator of the technical facility need access to various parts of the service software, for which reason the operator of the technical facility normally has access to the complete service software.

SUMMARY OF THE INVENTION

An object of the present invention is to allow more differentiated access to the service software of the technical facility.

This object is achieved in a technical facility having service software stored on a computer of the technical facility, the service software including first, second and third service modules. The first service module is allocated to a first service routine or a first group of service routines and is available to an operator of the technical facility without training for an application of the first service routine or the first group of service routines. The second service module is allocated to a second service routine or a second group of service routines and is available to the operator of the technical facility only after training for an application of the second service routine or of the second group of service routines. The third service module is allocated to a third service routine or a third group of service routines and is denied to the operator of the technical facility. The service software of the technical facility thus is divided into three service modules, i.e. into three levels. The first service routine or the first group of service routines of the first service module correspond to a first level and are available to the operator of the technical facility without previous training. This service routine or these service routines are program routines of the service software and are allocated, for example, to applications that, in particular, are also routinely implemented by the operator of the technical facility during its proper use and for which no specific training is necessary. These, for example, are regularly implemented quality checks, simple adjustment settings or the installation of a replacement part for which implementation no specific knowledge is required. The second service routine or the second group of service routines allocated to the second service module correspond to a second level and require training for being applied. This service routine or service routines are more complicated to apply than the first service routine or the first group of service routines. An application of the second service routine or of the second set of service routines can fundamentally be made available to the operator of the technical facility. Since their application, however, is more complicated than the application of the first service routine or the application of the first group of service routines, the operator is granted access to the second service routine or to the second group of service routines only when the operator has specifically trained personnel available. The third service routine or the third group of service routines allocated to the third service module and that thus correspond to the third level are completely denied to the operator of the technical facility. This service routine or these service routines are thus accessible only to the manufacturer or to a person or group of persons authorized by the manufacturer. It is thus assured that the operator has no access to specific service routines of the technical facility that are exclusively reserved for the manufacturer of the technical facility. One example of such a service routine is a remote service via a remote information transmission network. It also is assured that the operator only has access to that part of the service software for which specific training is needed when the operator has suitably trained personnel available.

So that only trained personnel belonging to the operator have access to the second service routine or the second group of service routines of the second service module, the second service routine or the second group of service routines of the second service module in an embodiment of the invention are available only by means of an identifier that can be entered into the computer of the technical facility. The operator, thus, is only informed of the identifier when his/her personnel are appropriately trained. The identifier, moreover, can also be valid for a limited time.

In a preferred embodiment of the invention different service routines of the second group of service routines of the second service module are available to the operator of the technical facility dependent on the type of training. Consequently, only those service routines of the second group of service routines for which the operator has appropriately trained personnel are available to the operator of the technical facility. The operator is also provided with the opportunity to decide what service routines of the second group the operator would like to apply, i.e. for which of these service routines the operator would like to have the operator's personnel trained. embodiment of the invention, the first service routine or the first group of service routines of the first service module is freely available to the operator of the technical facility.

An advantage of the inventive technical facility is the allocation of the service software functionalities to defined service routines. These, for example, can be accessed or implemented via the potentially limited-time identifiers, referred to as license keys. Specific access authorizations to parts of the service software thus can be designated for sale to a particular operator of the technical facility. Among others, the following advantages are achieved:

- reduction of the on-site activities of the supplier or manufacturer since operator's personnel can be designationally trained;
- on-site support of the supplier's own or, respectively, operator's own personnel by trained personnel belonging to the operator;
- enhanced customer linking by means of timed licensing;
- sales increase and market expansion by marketing the supplier's own or the manufacturer's own competency (training the operator's own personnel)
- additional sales increase from technical training and sale of replacement parts based on the increase in the size of the circle of customers or, respectively, tending to the technical personnel of the customer, i.e. of the operator of the technical facility.

DESCRIPTION OF THE DRAWINGS

FIG. 2 illustrates a structure of a service software stored on the technical facility shown in FIG. 1.

DESCRIPTION OF THE PREFERRED EMBODIMENTS

Figure 1:
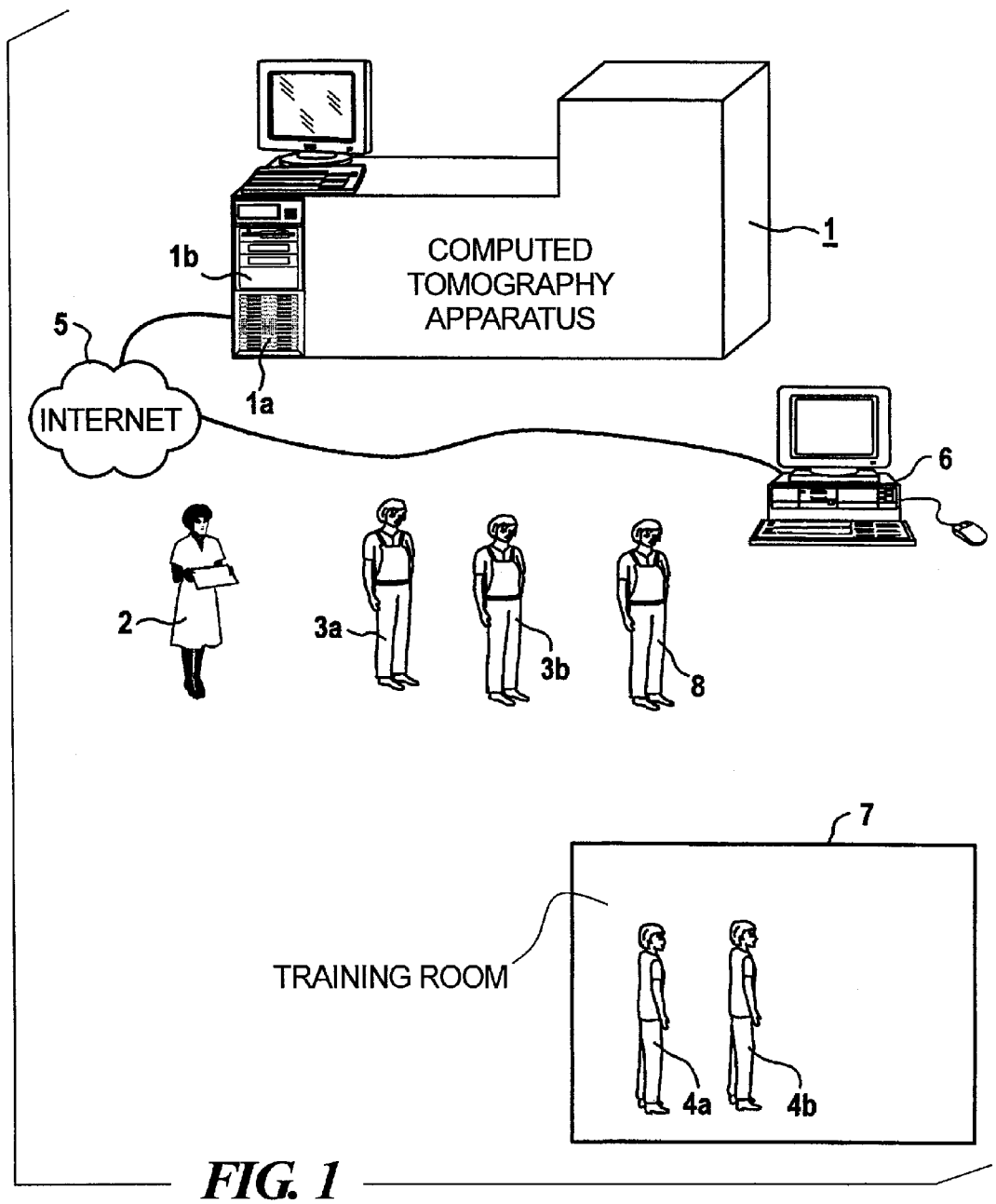
FIG. 1 schematically illustrates an inventive technical facility.

FIG. 1 shows a computed tomography apparatus 1 having a computer 1a. A computer program known to those skilled in the art runs in the computer 1a, the computer program suitably controlling the computed tomography apparatus 1 during an examination of a patient (not shown in FIG. 1).

Service software, the structure of which is schematically shown in FIG. 2, is also stored on the computer 1a. The service software is a computer program that is modularly constructed and has three service modules 21, 22 and 23. Each of the three service modules 21, 22 and 23 has a number of service routines, i.e. computer sub-programs of the service software, that are allocated to different service functions.

The service routines of the service module 21 are allocated to service functions the application of which requires no specific training. The operator's personnel can apply these service routines as soon as the computed tomography apparatus 1 is installed and ready to operate. An application of these service routines is possible without entering a specific identifier into the computer 1a. In the exemplary embodiment, moreover, the operator of the computed tomography apparatus 1 need not pay any licensing fees to the manufacturer of the computed tomography apparatus 1 for the use of the service routines of the service module 21.

Moreover, a license level L1 is allocated to the service routine or routines of the service module 21 in the exemplary embodiment.

The service module 21 has three service routines in the exemplary embodiment. On the basis of the first service routine of these three service routines, the operator's personnel such as, for example, a medical-technical assistant (MTA) 2, who operates the computer tomography apparatus 1 during an examination of the patient, or service technicians 3a and 3b working for the operator, can check the quality of images produced with the computed tomography apparatus 1. With the second service routine, it can display and evaluate the content of an error memory 1b of the computer 1a of the computed tomography apparatus 1 and, with the third service routine, it can load an application license onto the computer 1a of the computed tomography apparatus 1.

The service routines of the service module 22 are allocated to service functions for the application of which specific training is necessary. These service routines therefore are available only to the operator of the computed tomography apparatus 1 when the operator has appropriately trained personnel available. Training is optional and can be essentially undertaken at any time by the operator in the exemplary embodiment. As long as the operator has no suitably trained personnel available, the personnel of the operator cannot access the service routines of the service module 22, i.e. the service functions allocated to the service module 22 cannot be used as long as the operator does not have suitably trained personnel available.

In the exemplary embodiment, the service routines of the service module 22 are also divided into four groups. Each group of service routines is allocated to a license level, which are the license levels L2, L3, L4 and L5 in the exemplary embodiment.

The operator needs suitably trained personnel for each of these groups of service routines. When, however, personnel of the operator are trained for a higher license level, this personnel must already have been trained for the license levels lying therebelow. When, for example, personnel of the operator is trained for license level 4, then the personnel must already have been trained for license levels 2 and 3.

The operator must also pay specific licensing fees to the manufacturer for license levels L3 through L5 if the operator would like to use the service routines allocated to these license levels. The licensing fees are graduated in the exemplary embodiment, with a higher license level covering the license levels lying therebelow. When, for example, the operator pays licensing fees for license level L5, then the service routines allocated to the license levels L3 and L4 are also available to the operator. No licensing fees are required for license level L2 in the exemplary embodiment.

In the exemplary embodiment, license level L2 covers service routines with which a configuration of the computed tomography apparatus 1 is supported, the current configuration of the computed tomography apparatus 1 is displayed and simple tests and setting at the computed tomography apparatus 1 are supported.

The license levels L3 through L5 cover further service routines that can be applied for further service functions.

In the exemplary embodiment, the manufacturer offers the operator suitable training. Specifically trained technicians 4a and 4b of the manufacturer carry out the training in a training room 7 of the manufacturer. After successful participation in a training, the participants in the training receive a certificate that confirms the successful participation.

In the exemplary embodiment, the operator's service technician 3a successfully participated in the training for license level L2. The successful participation was confirmed. The operator was also informed of an identifier allocated to the service routines of license level L2 of the service module 22 so that the service routines of the license level L2 can be called and applied. Upon entry of this identifier into the computed 1a of the computed tomography apparatus 1, the service routines of the license level L2 of the service module 22 are available to the service technician 3a.

In the exemplary embodiment, the operator's service technician 3b successfully participated in a training for the service routines of the license levels L2 through L5. Consequently, the service technician 3b is suitably trained for an application of the service routines of the license levels L2 through L5 and can apply these. After the operator paid the necessary licensing fees to the manufacturer, the manufacturer informed the service technician 3b of a suitable identifier that, when entered into the computer 1a of the computed tomography apparatus 1, makes the service routines of the licensing levels L2 through L5 of the service module 22 available to the service technician 36.

The service module 23, finally, is reserved only for the manufacturer of the computed tomography apparatus 1 and cannot be released to the operator of the computed tomography apparatus 1. Only the manufacturer's own personnel such as a service technician 8 can call and apply these service routines. In the exemplary embodiment, the service module 23 has three service routines. The computed tomography apparatus 1 is automatically monitored by means of the first service routine of these three service routines. If an error of the computed tomography apparatus 1 occurs, the computer 1a generates an corresponding error message and—since it is connected to the Internet 5 in the exemplary embodiment—sends this message via the Internet 5 to a computer 6 of the manufacturer that is likewise connected to the Internet 5. The operator's service technician 8 can subsequently read and evaluate the error message. The service software can be serviced and may be modified with the second service routine. With the third service routine, the picture screen of the computer 1a of the computed tomography apparatus 1 can be mirrored at the picture screen of the manufacturer's computer 6 in order, for example, to be able to perform remote maintenance of the computed tomography apparatus 1.

The inventive technical facility thus offers a merging of the sale of service software access levels or service licenses with specific training of the customer's technical personnel, i.e. of the service technicians 3a and 3b of the operator of the computed tomography apparatus 1. In particular, the manufacturer of the technical facility carries this training out and can thus suitably adapt the educational objective and level of the operator's personnel who have been trained.

The service software is also hierarchically divided, with a higher license level covering the license levels lying therebelow. This assured that the operator, i.e. the customer, does not receive access to service routines that the operator need not apply.

Another advantage of the inventive technical facility is the promotion and linking of the customer-manufacturer partnership as a result of the training and certification. Further advantages include:

enhancing the customer dependency, particularly when the licensing is limited in time.

supporting the customer in terms of the customer's technical development based on optionally acquired service software licenses.

customer linking and market expansion by means of designational sale of competency.

The above-described exemplary embodiment, moreover, is to be understood as being only by way of example. In particular, the inventive technical facility is limited neither to a computer tomography apparatus 1 nor to a medical-technical apparatus in general.

Although modifications and changes may be suggested by those skilled in the art, it is the intention of the inventors to embody within the patent warranted hereon all changes and modifications as reasonably and properly come within the scope of their contribution to the art.

We claim as our invention:

1. A technical facility comprising:
    a facility device;
    a computer operable by an operator associated with said technical facility to operate said facility device under normal operating conditions;
    service software stored in said computer, necessary for servicing said facility device, differing from said normal operating conditions, said service software comprising a first service module for servicing said facility device, a second service module for servicing said facility device and a third service module for servicing said facility device;
    said first service module being allocated to a first service routine and being available to said operator associated with said technical facility without training for usage of said first service routine;
    said second service module being allocated to a second service routine and being available to said operator associated with said technical facility only after training for usage of said second service routine; and
    said third service module being allocated to a third service routine and access to said third service module being always denied to said operator associated with said technical facility.

2. A technical facility as claimed in claim 1, wherein said second service routine is available by entering an identifier into said computer.

3. A technical facility as claimed in claim 1 wherein said first service module makes said first service routine freely available to said operator associated with said facility.

4. A technical facility comprising:
    a facility device;
    a computer operable by an operator associated with said technical facility to operate said facility device under normal operating conditions;
    service software stored in said computer, necessary for servicing said facility device, differing from said normal operating conditions, said service software comprising a first service module for servicing said facility device, a second service module for servicing said facility device and a third service module for servicing said facility device;
    said first service module being allocated to a first group of service routines and being available to an operator of said technical facility without training for usage of said first group of service routines;
    said second service module being allocated to a second group of service routines and being available to said operator of associated with said technical facility only after training for usage of said second group of service routines; and
    said third service module being allocated to a third group of service routines and access to said third service module always being denied to said operator associated with said technical facility.

5. A technical facility as claimed in claim 4, wherein said second group of service routines is available by entering an identifier into said computer.

6. A technical facility as claimed in claim 4 wherein said first service module makes said first group of service routines freely available to said operator associated with said technical facility.

7. A technical facility as claimed in claim 4 wherein said second service module makes said service routines in said second group of service routines available associated with said technical facility to said operator respectively dependent on a type of training of said operator associated with said technical facility.

8. A method for operating a technical facility comprising the steps of:
   providing a computer at a technical facility operable by an operator associated with said technical facility for operating a facility device of said technical facility under normal operating conditions;
   storing service software in said computer necessary for servicing said facility device, differing from said normal operating, said service software comprising a first service module for servicing said facility device, a second service for servicing said facility device module and a third service module for servicing said facility device;
   allocating said first service module to a first service routine available to said operator associated with said technical facility without training for usage of said first service routine;
   allocating said second service module to a second service routine available to said operator associated with said technical facility only after training for usage of said second service routine; and
   allocating said third service module to a third service routine and always denying access to said third service module by said operator of said technical facility.

9. A method for operating a technical facility as claimed in claim 8, compromising making said second service routine available by entering an identifier into said computer.

10. A method for operating a technical facility as claimed in claim 8 compromising making said first service routine freely available to said operator associated with said technical facility via said first module.

11. A method for operating a technical facility comprising the steps of:
    providing a computer at a technical facility operable by an operator of said technical facility for operating facility device of said technical facility under normal operating conditions;
    storing service software in said computer necessary for servicing said facility device, differing from said normal operating, said service software comprising a first service module for servicing said facility device, and second service module for servicing said facility device and a third service module for servicing said facility device;
    allocating said first service module to a first group of service routines available to said operator associated with said technical facility without training for usage of said first group of service routines;
    allocating said second service module to a second group of service routines available to said operator associated with said technical facility only after training for usage of said second group of service routines; and
    allocating said third service module to a third group of service routines and always denying access to said third service module to said operator associated with said technical facility.

12. A method for operating a technical facility as claimed in claim 11, compromising making said second group of service routines available by entering an identifier into said computer.

13. A method for operating a technical facility as claimed in claim 11 compromising making said first group of service routines freely available to said operator associated with said technical facility via said first service module.

14. A method for operating a technical facility as claimed in claim 11 compromising making said service routines in said second group of service routines available to said operator associated with said technical facility via said second module respectively dependent on a type of training of said operator associated with said technical facility.

* * * * *